US009072434B2

(12) United States Patent
Thibos et al.

(10) Patent No.: US 9,072,434 B2
(45) Date of Patent: Jul. 7, 2015

(54) METHODS, SYSTEMS AND APPARATUSES FOR NIGHT AND DAY CORRECTIVE OPHTHALMIC PRESCRIPTION

(71) Applicant: INDIANA UNIVERSITY RESEARCH AND TECHNOLOGY CORPORATION, Indianapolis, IN (US)

(72) Inventors: Larry N. Thibos, Bloomington, IN (US); Jose Manuel Gonzalez-Meijome, Amares (PT); Norberto Lopez-Gil, Murcia (ES)

(73) Assignee: INDIANA UNIVERSITY RESEARCH & TECHNOLOGY CORPORATION, Indianapolis, IN (US)

( * ) Notice: Subject to any disclaimer, the term of this patent is extended or adjusted under 35 U.S.C. 154(b) by 0 days.

(21) Appl. No.: 14/463,093

(22) Filed: Aug. 19, 2014

(65) Prior Publication Data

US 2015/0009474 A1    Jan. 8, 2015

Related U.S. Application Data

(63) Continuation of application No. PCT/US2013/026868, filed on Feb. 20, 2013.

(60) Provisional application No. 61/600,844, filed on Feb. 20, 2012.

(51) Int. Cl.
*A61B 3/02* (2006.01)
*A61B 3/00* (2006.01)
(Continued)

(52) U.S. Cl.
CPC ............... *A61B 3/022* (2013.01); *A61B 3/028* (2013.01); *A61B 3/032* (2013.01)

(58) Field of Classification Search
USPC ................................................. 351/200–246
See application file for complete search history.

(56) References Cited

U.S. PATENT DOCUMENTS

| 4,943,151 A | 7/1990 | Cushman |
| 4,997,269 A | 3/1991 | Cushman |

(Continued)

FOREIGN PATENT DOCUMENTS

| JP | 11206709 | 8/1999 |
| JP | 20010087225 | 4/2001 |
| JP | 20050052677 | 3/2005 |

OTHER PUBLICATIONS

Lopez-Gil, Norberto et al., "Shedding Light on Night Myopia", Journal of Vision, May 15, 2012, 12(5):4, pp. 1-9.

(Continued)

*Primary Examiner* — Mohammed Hasan
(74) *Attorney, Agent, or Firm* — Faegre Baker Daniels LLP (57) ABSTRACT

One exemplary embodiment is a method for determining an ophthalmic prescription. An examination room is lighted to simulate daytime viewing and a conventional eye chart is used as a visual stimulus. A first corrective spherical lens power is determined by varying spherical lens power and identifying when perceived vision is best. The examination room is kept dark to simulate nighttime viewing conditions. The visual stimulus utilized is a white point source on a dark background, or a self illuminated symbol on a dark background. A second corrective spherical lens powered is determined by varying spherical lens power and identifying when perceived vision is best. An ophthalmic prescription such as one or more lenses, one or more surgical corrections or a combinations thereof is provided including a first corrective component including the first preferred spherical lens power, and a second corrective component including the second preferred spherical lens power.

20 Claims, 6 Drawing Sheets

(51) Int. Cl.
*A61B 3/028* (2006.01)
*A61B 3/032* (2006.01)

(56) References Cited

U.S. PATENT DOCUMENTS

| | | | |
|---|---|---|---|
| 5,223,866 A | | 6/1993 | Cushman |
| 7,364,299 B2 | | 4/2008 | Donnerhacke et al. |
| 8,882,264 B2 | * | 11/2014 | Bradley et al. ............ 351/159.05 |
| 2003/0020988 A1 | * | 1/2003 | Stone ............................ 359/159 |
| 2006/0238704 A1 | | 10/2006 | Donnerhacke et al. |
| 2008/0297723 A1 | | 12/2008 | Dai et al. |
| 2009/0251666 A1 | | 10/2009 | Lindacher et al. |

OTHER PUBLICATIONS

International Search Report and Written Opinion. PCT/US2013/026868, ISA/KR, Indiana University Research & Technology Corporation, Jun. 12, 2013.

Supplemental EPO Extended Search Report, European Patent Office, EP Appln. No. 13752391.6; Mar. 3, 2015, 8 pgs.

* cited by examiner

|  | Day Correction | Night Correction |
|---|---|---|
| 510 | Contact Lens | Contact Lens + Spectacle Lens |
| 520 | Spectacle Lens | Spectacle Lens + Clip-On Lens |
| 530 | Spectacle Lens | Spectacle Lens + Contact Lens |
| 540 | Surgical | Surgical + Spectacle Lens or Contact Lens |
| 550 | Compromise Spectacle Lens, Contact Lens, or Surgical | Compromise Spectacle Lens, Contact Lens, or Surgical |
| 560 | Day Spectacle | Night Spectacle |
| 570 | Day Contact Lens | Night Contact Lens |
| 580 | Spectacle Lens with Variable Power in Day Configuration | Spectacle Lens with Variable Power in Night Configuration |

Fig. 5

| | Night Correction | Day Correction |
|---|---|---|
| 610 | Contact Lens | Contact Lens + Spectacle Lens |
| 620 | Spectacle Lens | Spectacle Lens + Clip-On Lens |
| 630 | Spectacle Lens | Spectacle Lens + Contact Lens |
| 640 | Surgical | Surgical + Spectacle Lens or Contact Lens |

Fig. 6

METHODS, SYSTEMS AND APPARATUSES FOR NIGHT AND DAY CORRECTIVE OPHTHALMIC PRESCRIPTION

CROSS REFERENCE TO RELATED APPLICATIONS

The present application is a continuation of International Patent Application No. PCT/US2013/026868 filed on Feb. 20, 2013, which claims the benefit of the filing date of U.S. Provisional Patent Application 61/600,844 filed on Feb. 20, 2012, each of which is incorporated herein by reference in its entirety.

BACKGROUND

Some people experience greater levels of myopic refractive error (short-sightedness) at night compared to daytime vision. This disorder, known clinically as night myopia, was first described around the end of the 18th century by the presbyopic Royal Astronomer Reverend Nevil Maskelyne concerning his observations of distant stars without refractive correction as well as with daytime negative correction and slightly more negative lenses. A similar problem was noted almost a hundred years later in 1883 by Lord Rayleigh describing difficulties in identifying small objects under bad light conditions. Yet, more than two centuries later night myopia remains a poorly understood and enigmatic subject of study. A number of explanations for night myopia have been hypothesized Yet, in spite of these hypotheses, no definitive explanation for the aetiology of night myopia has been provided.

Reliable techniques for correction of night myopia could benefit many patients that experience reduced vision at night. Night myopia is a common patient complaint heard by practicing optometrists and is a recognized hindrance to safe nighttime driving and other nighttime activities. Heretofore there has been no reliable method or technique for determining the necessary adjustment to daytime prescriptions to correct for night myopia. Past attempts at providing such corrective prescriptions have been based on methods or explanations for night myopia such as the optics of the eye changing due to a larger pupil size, the presence of higher-order aberrations, an involuntary accommodative response produced under low lighting conditions, accommodation, or chromatic shift in scotopic light conditions.

Some past attempts to improve night vision, such as the approaches described in U.S. Pat. Nos. 4,943,151, 4,997,269 and 5,223,866, rely upon measuring dark focus acommodation of an eye under low ambient light levels or a refractive change between night and day lighting conditions with optometers in the hope of providing a better prescription. Other past attempts, such as the approach described in publication no. US 2003/0020988 A1, have proposed the prescription of lenses having some additional negative lens power, for example, between −0.12 to −1.00 diopters, based upon a trial and error approach. Further past attempts, such as that described in U.S. Pat. No. 7,364,299, rely upon objective, instrument-based measures of visual function such as measurements of mesopic vision and abberation.

The foregoing and other conventional attempts to improve night myopia have been hindered in part by incomplete and incorrect explanations for the causes of or factors contributing to this affliction. One explanation posits that uncorrected myopia or deliberate under-correction of myopia produced by maximum-plus refractions is less noticeable during the day when high levels of ambient luminance reduce the size of the eye's pupil, thereby reducing the amount of blur on the retina. Another explanation assumes that most eyes have positive spherical aberration (SA) when accommodation is relaxed which means the optical power of the eye is greater at the pupil margin than at the pupil center implying that the visual effects of spherical aberration will be most noticeable under dim illumination conditions. A further explanation is that optical image quality in any optical system exhibiting SA can be improved by a judicious change of focus. Yet another mechanism posited to contribute to night myopia arises for very dim (scotopic) illumination levels for which the fovea is blind. These and other conventional theories and explanations have proven to be at best incomplete and sometimes incorrect.

Existing attempts to improve night vision suffer from a number of limitations and drawbacks. They fail to account for the preference of the observer or visual performance in a vision test. They rely upon trial and error and are based on theory that is at best incomplete if not outright mistaken. They do not consider or account for the type or nature of visual stimulus encountered by a patient. They are based upon inadequate and incompletely defined metrics and definitions of improved vision and incomplete or incorrect explanations for the causes and factors contributing to night mypoia. These and other shortcomings have left the state of the art for improving night vision unsatisfactory to many patients and clinicians. There remains a longfelt need for the unique and inventive methods, systems, and apparatuses disclosed herein.

DISCLOSURE OF EXEMPLARY EMBODIMENTS

For the purposes of summarizing and clearly, concisely and exactly describing in detail exemplary embodiments of the invention, the manner and process of making and using the same, and to enable the practice, making and use of the same, reference will now be made to a number of exemplary embodiments including those illustrated in the figures and specific language will be used to describe the same. It shall nevertheless be understood that no limitation of the scope of the invention is thereby created, and that the invention includes and protects such alterations, modifications, and further applications of the exemplary embodiments as would occur to one skilled in the art to which the invention relates.

SUMMARY

One exemplary embodiment is a method for determining an ophthalmic prescription to improve vision at night. The method employs lenses of different power (e.g. ophthalmic trial lenses or a phoropter), or a variable power system (e.g. a Badal optometer). A unique testing protocol is utilized. In one part of the testing, the room is kept light to simulate daytime viewing conditions and a conventional eye chart is used as a visual stimulus. The clinician determines a first preferred spherical lens power by varying spherical lens power and asking the patient to subjectively report when perceived vision is best based upon specified criteria. The starting point for this procedure is the patient's existing prescription, or if that is not available, a distance prescription obtained by ordinary clinical methods. Astigmatism is an optical flaw of the eye unrelated to night myopia and therefore may be determined and corrected by ordinary clinical methods. In another part of the testing, the room is kept dark to simulate nighttime viewing conditions for which the eye's pupil is dilated. The visual stimulus utilized is a white point source on a dark background, or a self illuminated letter (or any other symbol)

on a dark background. The clinician determines a second preferred spherical lens power by varying spherical lens power and asking the patient to subjectively report when perceived vision is best based upon specified criteria. An ophthalmic prescription is provided including a first corrective component including the first preferred spherical lens power, and a second corrective component including the second preferred spherical lens power.

An ophthalmic prescription may be provided in a number of forms. In one form separate spectacle lenses or contact lenses for day and night vision, respectively, are provided. In another form a contact lens for day vision plus an additional spectacle lens for night vision to be utilized in combination with the contact lens is provided. In a further form a spectacle lens for day vision plus an additional contact lens for night vision to be utilized in combination with the spectacle lens is provided. In another form a spectacle lens is provided for day vision and an additional clip-on lens is provided to be used in combination with the spectacle lens for night vision. In another form a lens with continuously variable power (such as a fluid-filled lens, or a liquid-crystal lens) is set at one power for daytime viewing and another power for nighttime viewing. In an additional form a surgical correction such as LASIK is provided for day vision and an additional contact lens or spectacle lens is provided for night vision. In a further form a compromise prescription comprising a spectacle lens, a contact lens or a surgical correction including a compromise spherical power between a preferred night spherical power and a preferred day spherical power is provided. Further embodiments, forms, objects, features, advantages, aspects, and benefits shall become apparent from the following description and drawings.

DETAILED DESCRIPTION

Figure 1:
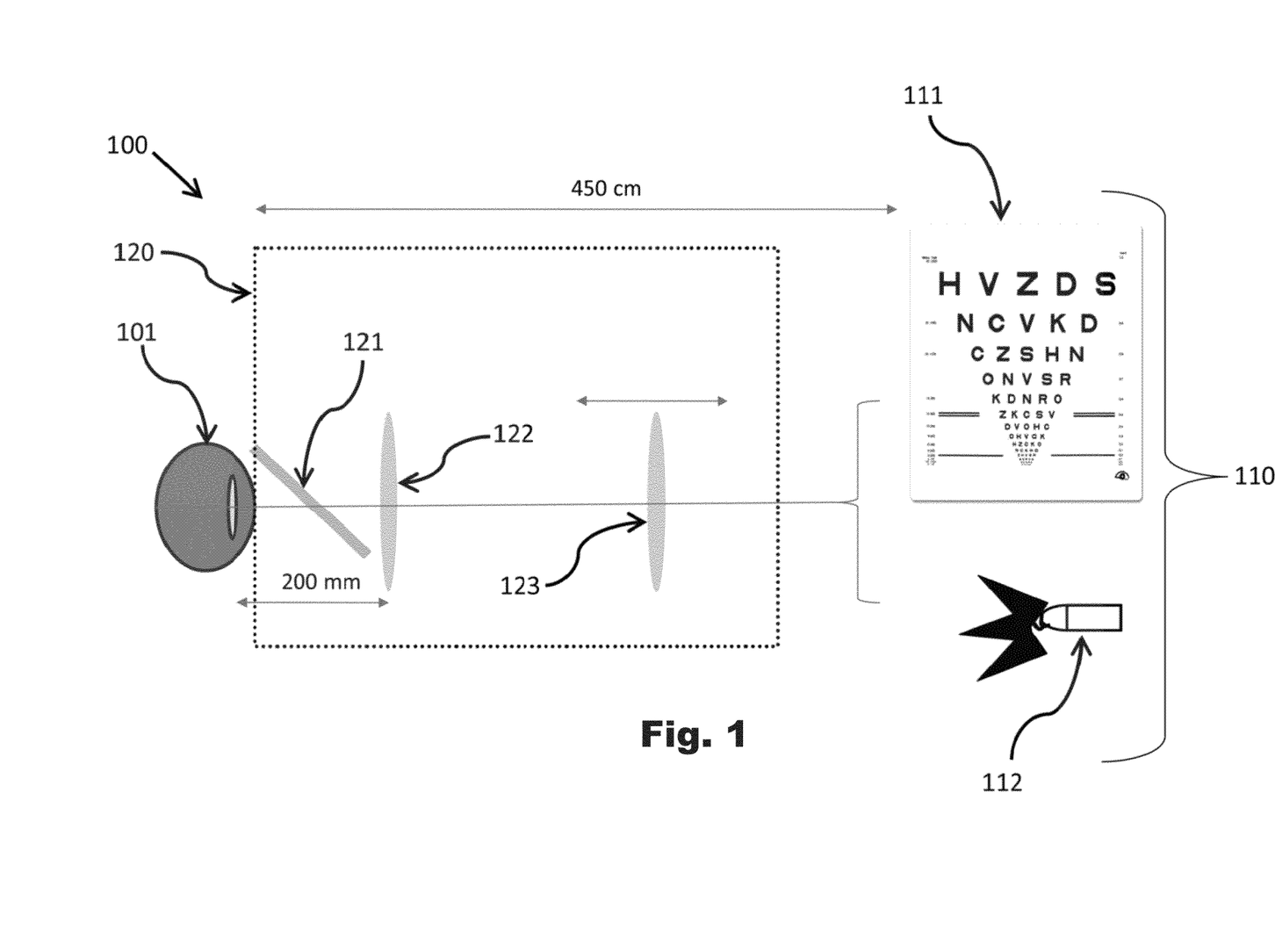
FIG. 1 illustrates an exemplary testing system.

With reference to FIG. 1 there is illustrated an exemplary system 100 for determining corrective prescriptions for a patient's eye 101 affected by night myopia. System 100 includes visual stimuli 110, lens system 120 and measurement instrumentation 130. In the illustrated embodiment, visual stimuli 110 include an ETDRS chart 111 and a 2 mm diameter white LED point source 112. Lens system 120 is a Badal lens system including a hot mirror 121, a fixed Badal lens 122 (having f'=200 mm) and a moving lens 123 (having f'=190 mm) Measurement instrumentation 130 is an autorefractometer or a wavefront aberrometer.

It shall be appreciated that a number of additions, alternatives and modifications to system 100 may be used in various embodiments. For example, a lens system may comprise a series of trial lenses such as provided by a phoropter or a lens with adjustable power placed some distance (for instance 12 mm) in front of the corneal vertex of the eye to be evaluated. An adjustable power lens may be constructed using a variety of technologies, such as a fluid-filled lens, or a liquid crystal lens, or an Alvarez lens, or a deformable mirror. An aberrometer, which has the potential to make objective measurements, may be used as an alternative to or in addition to the subjective judgments expected of patients as described herein and that the same or similar visual stimuli may be used in connection with objective aberrometer-based measurements. In a preferred form, the aberrometer readings are interpreted in accordance with the techniques set forth in U.S. Pat. No. 7,857,451. System 100 could also include twin systems of lenses in order to allow for simultaneous evaluation of both eyes. In this example, both systems might be adjusted simulaneously or separately, while keeping both eyes seeing the target stimulus or occluding one of the eyes.

System 100 may be utilized in connection with providing night and day corrective ophthalmic prescriptions for patients. In situations where a patient has an existing prescription, any previously identified refractive correction is incorporated into the system as a starting value. The patient is situated at a distance (e.g. 4 to 6 meters) from the visual stimuli and a measurement process is performed for each eye independently, while the other eye remains closed or is fogged.

During one operation of the measurement process, the patient is asked to observe a letter of the letter chart in an illuminated room that produces daylight levels of luminance. In one form substantially daylight levels of luminance are understood to be levels>50 $cd/m^2$, though it shall be understood that alternate definitions may apply in other forms. The patient or a clinician adjusts the power of the lens system to obtain the most positive value for which the subject can see the letter as clear as possible. This daytime spherical refraction may be recorded in diopters and is denoted P1.

Another operation of the measurement process is performed in a completely dark or a very dimly lit room (e.g. <0.1 $cd/m^2$ ambient luminance). In this operation the patient is again asked to observe a visual stimulus and report a subjectively preferred amount of correction. The visual stimulus used for this operation is a point source, for example a small white LED, or a self-luminous extended object such as a letter or other symbol which can even be displayed on a computer screen. A self-luminous object can also be produced by transillumination of an aperture having the shape of a letter or symbol. A common feature of these stimuli is the background for the stimulus is dark. This may be provided, for example, with the LED or the self-luminous object placed in a black box or against a black background that reflects negligible ambient light. Other arrangements that provide an object of high contrast may also be utilized such as back-illumination of mask that blocks all light except that which is transmitted by a letter-shaped aperture. The spherical refraction of this operation may be measured in diopters and is denoted P2 which indicates the spherical correction needed by the patient to see clearly at night. P2−P1 corresponds to a degree of night myopia.

During research and development leading to the present application, the inventors carried out clinical testing for seventeen emmetropic patients (spherical equivalent refractive error<±0.375 D) and two myopic patients corrected with contact lenses. The patient's age range was 21.9±4.6 years and their astigmatism (which was less than 0.75 D of cylindrical power as determined by subjective refraction) was left uncorrected. In all patients night myopia, P2−P1, was negative, indicating the presence of night myopia. The average value found was −0.91 D with a standard deviation of 0.52 D.

The research and development testing was carried out with a system generally in aconcordance with system 100 described above in connection with FIG. 1 The system included a Badal lens and a moving lens (L) which enabled the patient to adjust the stimulus vergence to maximize perceived quality. The resolution of the optimum target vergence measurements was 0.20 diopters.

Two types of visual stimuli were used during this clinical testing. One stimulus was a point source, specifically a white light-emitting diode (LED), angular subtense 0.86 arcmin, intensity 70 mcd. Another stimulus was an ETDRS letter chart displaying high-contrast, black letters on a white background and having a background luminance=200 cd/m$^2$. The luminance spectra of the LED and the letter chart were both similar when multiplied by the human spectral sensitivity function (V-lambda), which indicates negligible chromatic refractive shift between the two stimuli. During data collection the room was darkened to simulate night viewing conditions with a naturally dilated pupil.

The inventors research and development work yielded a number of surprising and inventive results. For example, surprising benefits were realized through the provision of an self-illuminated second stimulus such as a small letter or symbol presented against a dark background. The symbol can be self-illuminated or trans-illuminated in a number of manners as described herein. Multiple measurements to determine corrective ophthalmic prescriptions utilizing visual stimuli including a reversal of contrast, for example both black on white and white on black, yielded surprising advantages.

Figure 2:
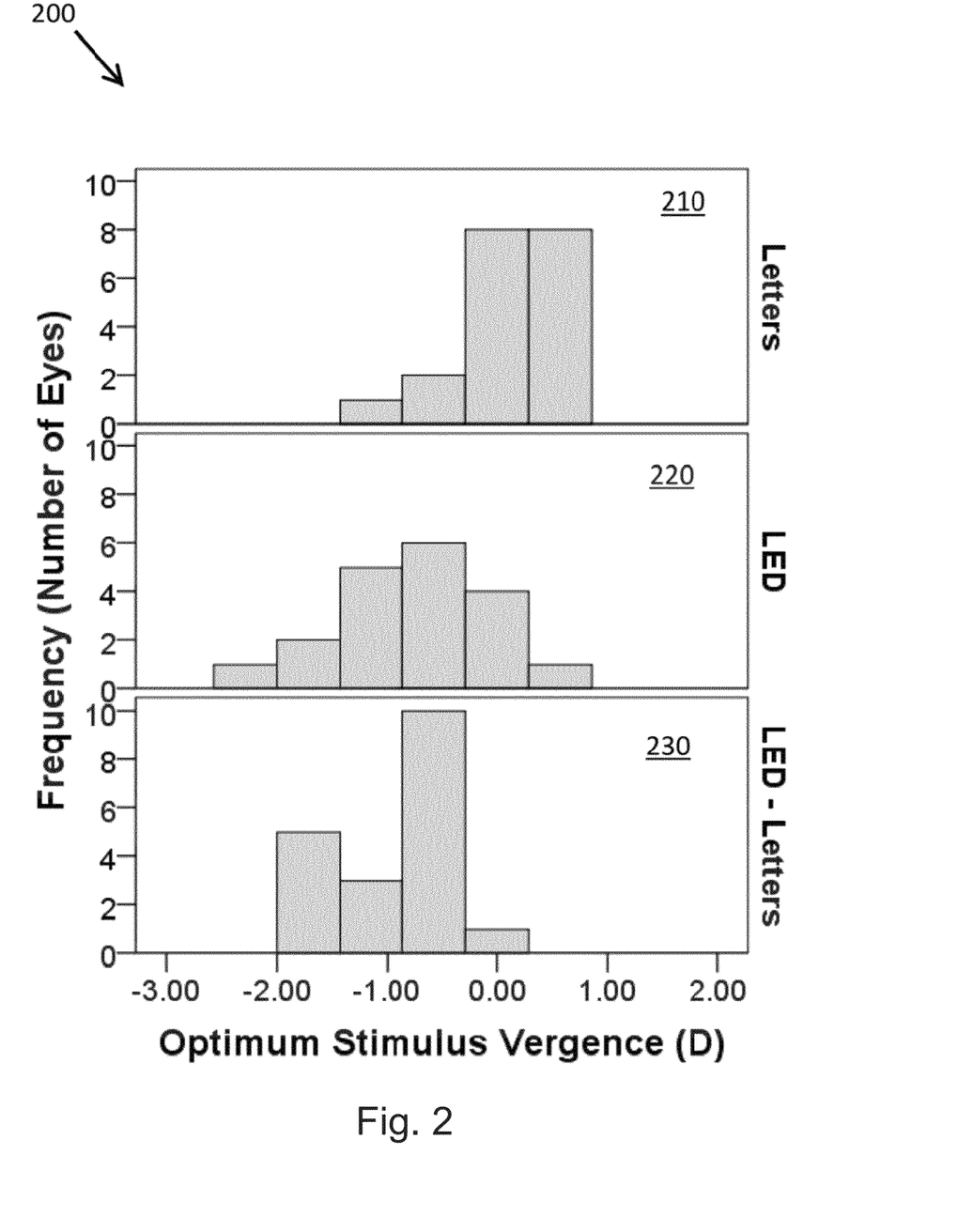
FIG. 2 illustrates frequency histograms of optimum stimulus vergence measured subjectively with a Badal optometer for a letters chart, an LED point source, and the difference between the LED point source and the letters chart.

FIG. 2 illustrates frequency histograms 200 of the optimum stimulus vergence measured subjectively with a Badal optometer for letters (histogram 210), LED (histogram 220) and the difference between them (histogram 230). Optimum refractive state (indicated by optimum stimulus vergence) for all eyes was more myopic (i.e. the eye had larger equivalent power) for the LED stimulus than for the letter-chart. Only one eye showed a similar refractive state for the two stimuli. Although our subject population was nominally emmetropic by clinical standards, the population mean of optimum refractive state was slightly hypermetropic (0.09 D, standard deviation=0.46) for the letter stimulus and significantly myopic (−0.81 D, standard deviation=0.64) for the point stimulus. To factor out individual differences in refractive errors for the population, we computed for each eye the difference between optimum refractive states for these two stimuli. The mean difference was 0.91 D (stdev=0.52) more myopic for the point stimulus compared to the letters. In other words, the refractive state of the average eye in our test population was significantly and surprisingly more myopic when perceived quality was optimized for the point stimulus compared to the letter stimulus.

As mentioned above, the inventors' research and development efforts have led to a number of important and surprising discoveries. In this regard the inventors have identified and established the importance of the nature and configuration of the visual stimulus and criterion when determining the optimum refractive state for maximizing perceived retinal image quality in the accommodating eye. When a point source is judged to be optimally focused according to the criteria of minimum image size and maximum contrast its vergence will be more negative than the vergence of an optimally focused letter chart according to the criterion of letter legibility. Thus, the eye's optimum refractive state for point sources is myopic relative to the optimum refractive state for letters under the conditions of our experiment. From this unexpected result it can be inferred that the night myopia phenomenon or part of it, can be explained if the optimum daytime refractive state is determined by letter chart legibility whereas the optimum nighttime refractive state is determined by point sources.

Light from objects at night is different from daylight. For example, contrast values and maximum luminance of self-luminous objects at night (such as LEDs, car lights, etc.) are much higher than most of the objects seen during the day. Additionally, tails of the light distribution for point sources can be much more visible with a dark background because of increased contrast. Thus, high-order aberrations, such us spherical aberration, may play a more important role at night than during the day, not only because of larger pupil diameter, but also because of larger contrast since their effects would be better appreciated by a visual system with a certain contrast threshold. As a simple example, the reader could look at a distant point source such an LED from an electronic device (TV, computer) in a relatively dark room through a +2 D lens added to his/her correction, in case of ametropia. The LED point should be seen as a relatively large and round defocused spot with a certain structure with bright and dark zones. Then, if the room light is suddenly switched on, the large blur circle will decrease leaving a much smaller defocused visualization of the LED. The effect is appreciated from the very first moment before the pupil has time to constrict, but the same effect can be appreciated with a mydriatic pupil.

In the case of an emmetropic eye, the larger contrast in the dark room makes the effect of the high-order aberrations much more visible than under daylight conditions when contrast is reduced. Thus, one aspect of a strategy for optimizing retinal image quality at night would be for the eye to reduce its spherical aberrations by accommodating, assuming the defocus generated by the accommodation can be compensated by an external focusing system (such as a telescope, spectacles, etc.).

Figure 3:
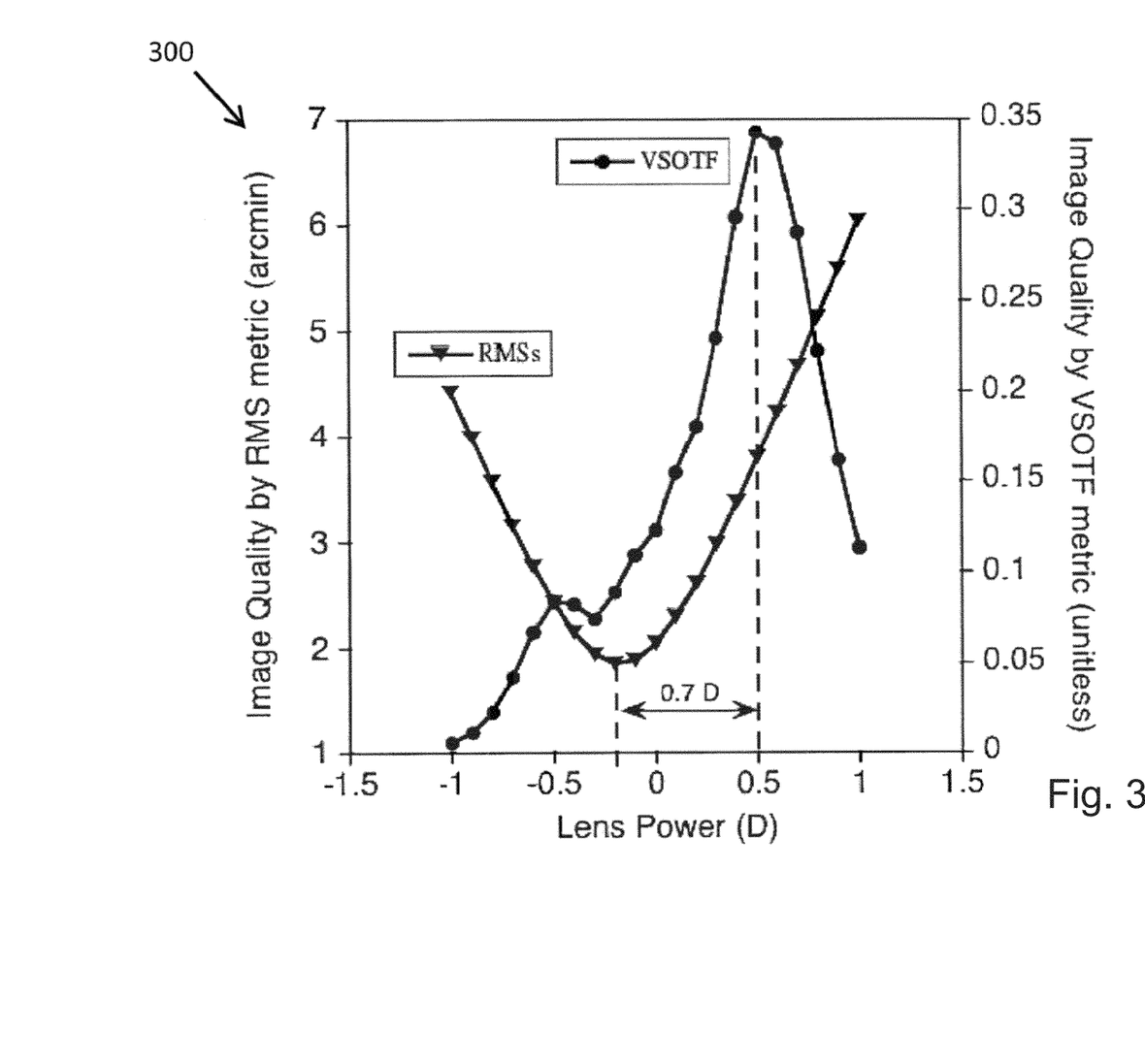
FIGS. 3 and 4 are graphs illustrating an effect of spherical aberration on optimum refractive state as determined by two different metrics of retinal image quality.

The inventors identified the correlation between SA of the relaxed eye and the magnitude of the myopic shift for point sources illustrated in FIG. 3 as a potential causal relationship. This possibility was evaluated theoretically by computing retinal image quality as a function of defocus and SA in an eye model with a 6 mm pupil that is otherwise free of monochromatic aberrations. To capture the difference between the two visual stimuli and their corresponding optimum vergence, two metrics of image quality were computed for each configuration of the model. The first metric, called RMSs, is defined as the root-mean-squared value of wavefront slopes over the domain of the eye's pupil. This metric represents the size of the image of a point source according to geometrical optics. The second metric is called visual Strehl ratio computed in frequency domain (VSOTF), which is defined as the volume under the visually weighted optical transfer function of the aberrated model, normalized by the volume under the visually weighted optical transfer function of the ideal, diffraction-limited model. This metric accurately predicts the legibility of letter stimuli and visual acuity.

FIG. 3 depicts a graph illustrating effect of defocus on optical quality of a theoretical eye model containing only positive spherical aberration ($C_4^0$=0.3 microns, 6 mm pupil diameter). Refractive state is the lens power that maximizes image quality (e.g. minimizes metric RMSs or maximizes metric VSOTF). The difference in refractive states for these two metrics is 0.7 D for this eye model. In a diffraction limited optical system, both metrics of retinal image quality change equally for equal amounts of positive and negative defocus. However, as shown in FIG. 3, when positive SA is introduced into the model, the minimum size of the image of a point (as specified by metric RMSs) occurs when the eye model views through a defocusing lens with negative power (−0.2 D) and therefore the eye model would be characterized as myopic. The opposite behavior occurs for the image quality metric VSOTF that is appropriate for letter stimuli. The maximum value of metric VSOTF occurs when the eye model views through a defocusing lens with positive power (+0.5 D) 5 and therefore the eye model would be characterized as hyperopic. Thus for this eye model, there is a significant difference of refractive state (0.7 D) for the two visual stimuli according to appropriate metrics of image quality, with point sources yielding the more myopic state.

Figure 4:
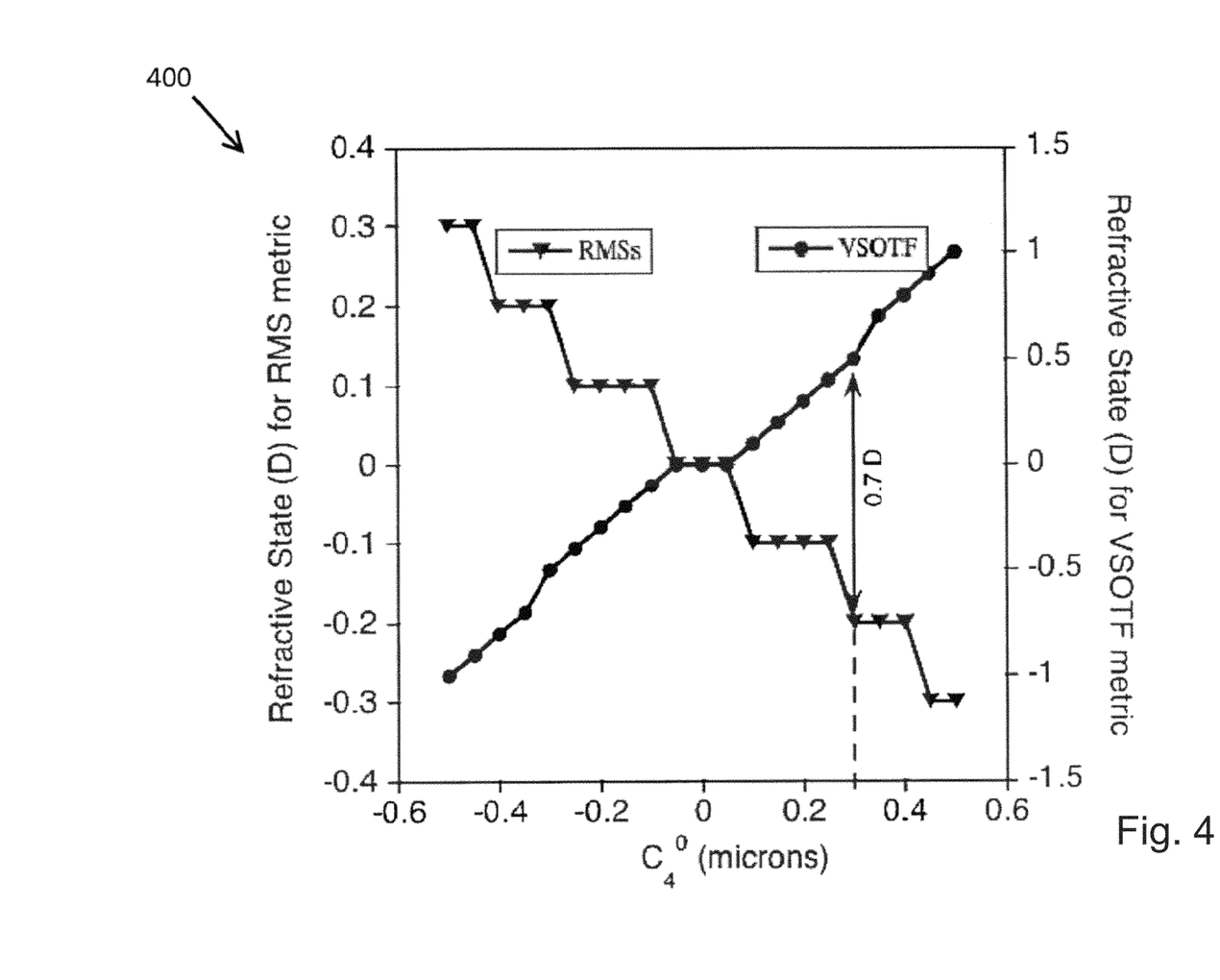

FIG. 4 illustrates the effect of spherical aberration on optimum refractive state as determined by two different metrics of retinal image quality. Each symbol represents the optimum stimulus vergence obtained from a through-focus graph of the type shown in FIG. 3. Amount of spherical aberration is specified by Zernike coefficient $C_4^0$. As illustrated in FIG. 4, the refractive state of the eye model for the two metrics RMSs and VSOTF varies with the amount of spherical aberration. The difference in refractive state predicted for the two metrics grows increasingly larger as the magnitude of spherical aberration increases and the relative sign of this difference in refractive state depends on the sign of the spherical aberration.

To interpret these foregoing data and calculations, the inventors considered an eye with relaxed accommodation for which spherical aberration is maximally positive. Had this eye failed to accommodate to changes in stimulus vergence, then we would have expected the patient to adjust the Badal stimulator to provide additional negative vergence when viewing a point source, but provide additional positive vergence when viewing a letter chart. That prediction is consistent with the sign of the results obtained experimentally as shown in FIG. 2.

The patient's eye in case of being non presbyopic can accommodate to some degree, so according to FIG. 4, the difference in optimum refractive state obtained for the two stimuli is less than would have been obtained in the absence of accommodation. Indeed, knowing that spherical aberration decreases with accommodation, had the patients accommodated sufficiently to eliminate spherical aberration entirely, the optical model predicts zero difference in optimum refractive states for the two stimuli. This indicated that the patients accommodated less than would have been needed to completely eliminate the spherical aberration of their eyes. The inventors' experimental results revealed about half of the 0.9 D difference in refractive state measured for the two visual stimuli could be accounted for by accommodation. The remaining half attributed to the effects of spherical aberration is of the same order as the difference in refractive state predicted by an eye model for levels of spherical aberration encountered in the inventors test population of eyes.

To gain a deeper understanding of why the optimum refractive state should depend on the visual stimulus, the inventors considered a slightly myopic astronomer viewing a bright star through a telescope focused on infinity. If a normally aberrated eye has positive spherical aberration, the retinal image will have a starburst appearance with a central core and radiating tails that are visible against a dark background. These tails are a perceptual cue that the image is not well focused, which prompts an adjustment of the focus of the telescope to eliminate the tails. Adding negative vergence will compensate for the negative vergence required when the eye has positive spherical aberration. Thus the eye will appear to have been over-corrected by the telescope, indicating a larger degree of myopia than would have been present without spherical aberration. Now reverse the stimulus contrast by using small dark objects on a bright background, such as black letters on white paper. The tails of individual points of light on the paper produce insufficient contrast to be visible on the light background, but will combine to increase the luminance of the dark letters. This loss of contrast is a perceptual cue that the image is not well focused, which prompts an adjustment of the focus of the telescope to increase contrast. However, the optical calculations summarized in FIG. 4 indicate that the adjustment should be less than that required without spherical aberration. The reason is that the increased contrast achieved by adding additional negative vergence is accompanied by contrast reversals and possibly other spatial phase shifts in the image that hamper legibility. Thus the optimum stimulus vergence for dark objects on a light background occurs when the target vergence is less negative than for point sources on a dark background.

From the foregoing analysis the inventors have identified that phase shifts induced by defocus in the presence of spherical aberration strongly influence the legibility and perceived quality of high-contrast daytime-objects such as dark letters on a bright background. When spherical aberration is positive, the under-powered eye is plagued by spatial phase shifts whereas the over-powered eye avoids these phase shifts. Thus, an optimum spectacle correction prescribed for daytime viewing of high contrast letters leaves the eye slightly over-powered (i.e. under-corrected myopia). When the same correction is used at night to view bright sources on a dark background, under-correction leads to starburst patterns that demand more negative power in the correcting lenses, and thus a tendency for night myopia. Thus, the inventors have established that subjective refractive error is influenced by stimulus configuration. Stimuli typically encountered at night leave the eye in a more myopic state compared to daytime targets.

Figure 5:
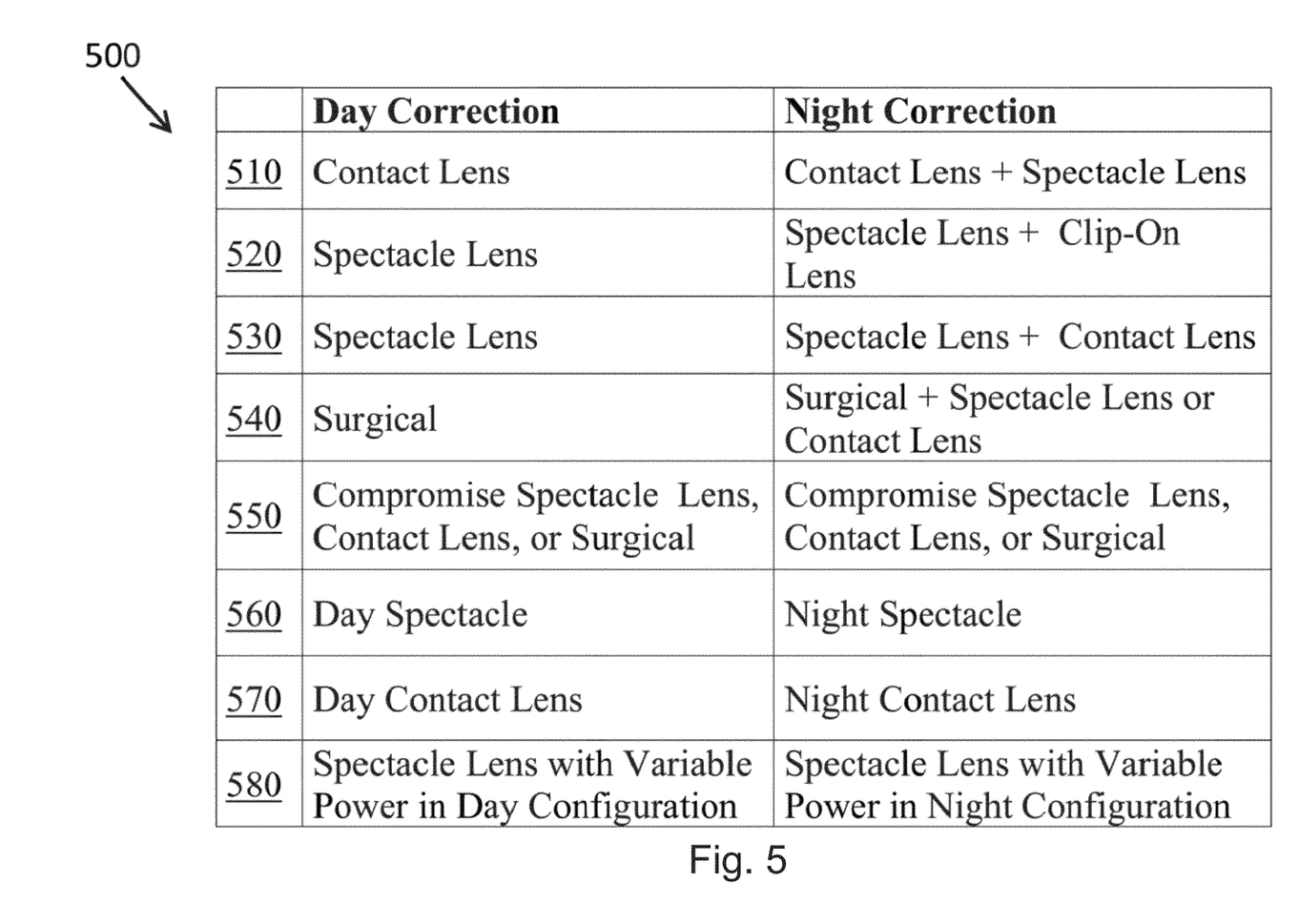
FIGS. 5 and 6 are tables illustrating a number of exemplary corrective ophthalmic prescriptions for night myopia.

The inventors' research and theory development has led to and forms the foundation for a number of significant real world advances in patient care. For example, FIG. 5 illustrates table 500 summarizing a number of exemplary day and night corrective ophthalmic prescriptions. It shall be appreciated that the terms prescription and correction each refer to one or more tangible articles or surgical acts rather than to an abstract concept. Ophthalmic prescription 510 comprises a contact lens for day vision and a spectacle lens for night vision to be utilized in combination with the contact lens. Ophthalmic prescription 520 comprises a spectacle lens for day vision and a clip-on lens to be used in combination with the spectacle lens for night vision. Ophthalmic prescription 530 comprises a spectacle lens for day vision and a contact lens for night vision to be utilized in combination with the spectacle lens. Ophthalmic prescription 540 comprises a surgical correction for day vision and a contact lens or spectacle lens for night vision. Ophthalmic prescription 550 comprises a spectacle lens, a contact lens or a surgical correction including a compromise spherical power between a preferred night spherical power and a preferred day spherical power. Ophthalmic prescription 560 comprises separate spectacle lenses for day and night vision, respectively. Ophthalmic prescription 570 comprises separate contact lenses for day and night vision, respectively. Ophthalmic prescription 580 comprises a spectacle lens with variable power which can be altered or controlled to assume a day correction configuration and a night correction configuration.

Figure 6:
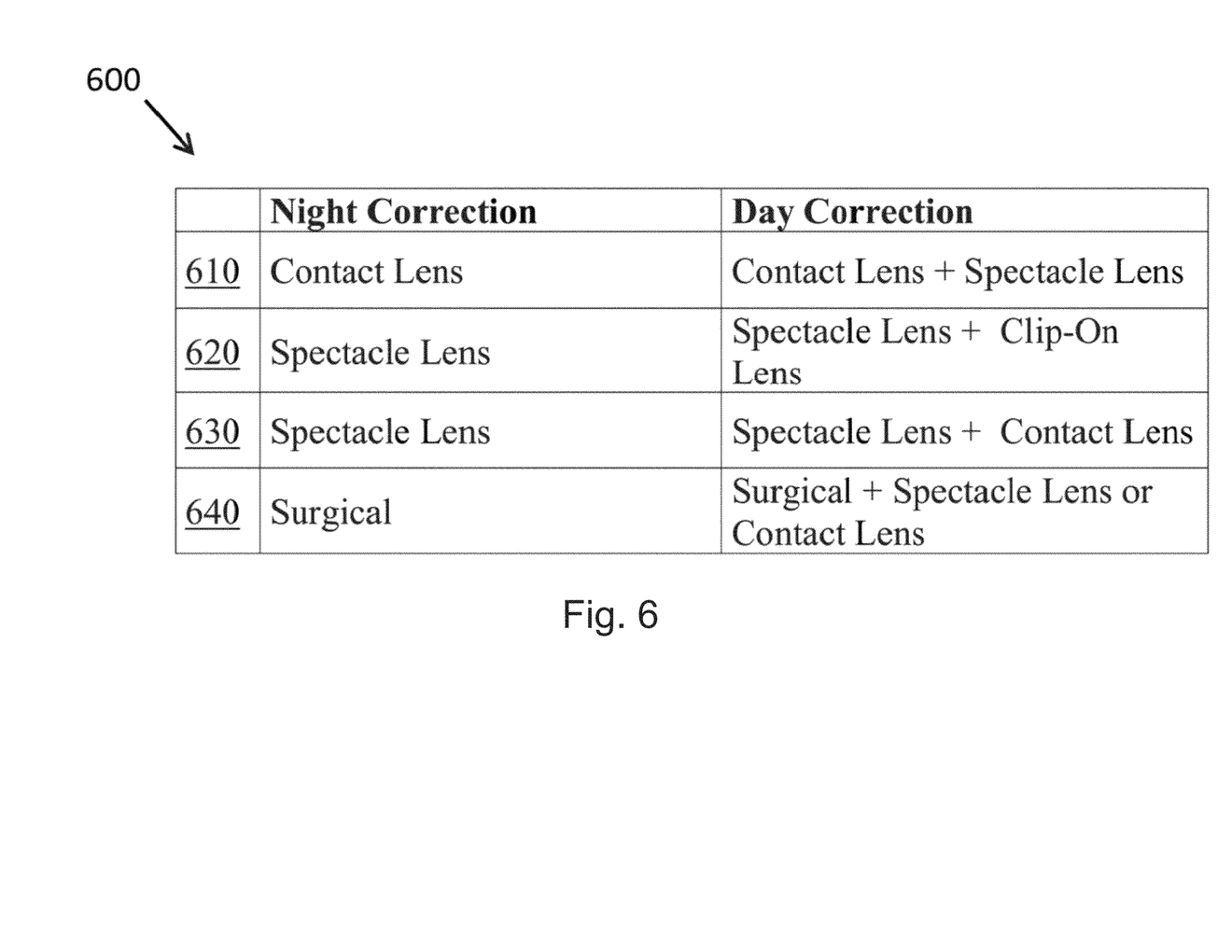

FIG. 6 illustrates table 500 summarizing a number of exemplary day and night corrective ophthalmic prescriptions. Prescriptions 610, 620, 630, and 640 are analogous to prescriptions 510, 520, 530, and 540; however the day and night corrective techniques have been juxtaposed. Thus, ophthalmic prescription 610 comprises a contact lens for night vision and a spectacle lens for day vision to be utilized in combination with the contact lens. Ophthalmic prescription 620 comprises a spectacle lens for night vision and a clip-on lens to be used in combination with the spectacle lens for day vision. Ophthalmic prescription 630 comprises a spectacle lens for night vision and a contact lens for day vision to be utilized in combination with the spectacle lens. Ophthalmic prescription 640 comprises a surgical correction for night vision and a contact lens or spectacle lens for day vision.

It shall be understood that the exemplary embodiments summarized and described in detail above and illustrated in the figures are illustrative and not limiting or restrictive. Only the presently preferred embodiments have been shown and described and all changes and modifications that come within the scope of the invention are to be protected. It should be understood that various features and aspects of the embodiments described above may not be necessary and embodiments lacking the same are also protected. In reading the claims, it is intended that when words such as "a," "an," "at least one," or "at least one portion" are used there is no intention to limit the claim to only one item unless specifically stated to the contrary in the claim. When the language "at least a portion" and/or "a portion" is used the item can include a portion and/or the entire item unless specifically stated to the contrary.

The invention claimed is:

1. A system for determining a corrective ophthalmic prescription comprising: a variable lens system including a line of sight from an eye location to a variable visual stimulus, the variable visual stimulus variable between a first visual stimulus and a second visual stimulus, the system configured to vary the spherical lens power along the line of site, the system being configurable in a first state providing daytime viewing conditions for the first visual stimulus wherein the first visual stimulus is ambiently illuminated, and a second state providing nighttime viewing conditions for the second visual stimulus wherein the second visual stimulus is self-illuminated.

2. A system according to claim 1, wherein the first visual stimulus comprises an ambiently illuminated eye chart.

3. A system according to claim 1, wherein the first visual stimulus comprises a diffusely reflecting object illuminated from the front.

4. A system according to claim 1, wherein the first visual stimulus comprises an ambiently illuminated ETDRS chart.

5. A system according to claim 1, wherein the second visual stimulus comprises a point source of light.

6. A system according to claim 5, wherein the point source of light comprises a colored LED.

7. A system according to claim 5, wherein the point source of light comprises a white LED.

8. A system according to claim 5, wherein the point source of light is provided on a dark background.

9. A system according to claim 1, wherein the second visual stimulus comprises a self-illuminated symbol or shape.

10. A system according to claim 9, wherein the self-illuminated symbol or shape is provided on a dark background.

11. A method of providing a corrective ophthalmic prescription comprising:
providing daytime viewing conditions and identifying a first preferred spherical lens power based upon first information of a patient viewing a first visual stimulus while varying spherical lens power;
providing nighttime viewing conditions and identifying a second preferred spherical lens power based upon second information of the patient viewing a second visual stimulus while varying spherical lens power; and
providing an ophthalmic correction including a first corrective component based upon the first preferred spherical lens power, and a second corrective component based upon the second preferred spherical lens power.

12. A method according to claim 11, wherein the first visual stimulus comprises a diffusely reflecting object illuminated from the front and the second visual stimulus comprises at least one of a point source of light and a self-illuminated symbol or shape.

13. A method according to claim 11, wherein the first preferred spherical lens power is selected based upon first subjective feedback from the patient that a first criterion of letter legibility has been satisfied, and the second preferred spherical lens power is selected based upon second subjective feedback from the patient that a second criterion of minimum image size and maximum contrast have been satisfied.

14. A method according to claim 11, wherein the first information of a patient comprises a first instrument measurement and the second information of a patient comprises a second instrument measurement.

15. A method according to claim 11, wherein the varying spherical lens power is performed by one of a power adjustable system integrated by a monocular system, a power adjustable system integrated by a twin system for binocular simultaneous adjustment and a power adjustable system integrated by alternating adjustment while both eyes are seeing the same visual stimulus.

16. A method according to claim 11, wherein the ophthalmic correction comprises a first corrective component structured to provide a first spherical lens power, said first spherical lens power being of a first magnitude selected to provide first correction of a patient's vision meeting a first predetermined criteria under daytime viewing conditions of a first predetermined visual stimulus, and a second corrective component structured to provide a second spherical lens power, said second spherical lens being of a second magnitude selected to provide second correction of a patient's vision meeting a second predetermined criteria under nighttime viewing conditions of a second predetermined visual stimulus.

17. A method according to claim 11, wherein the first corrective component comprises a spectacle lens and the second corrective component comprises a clip on lens.

18. A method according to claim 11, wherein the first corrective component comprises a contact lens and the second corrective component comprises a spectacle lens.

19. A method according to claim 11, wherein the first corrective component comprises a spectacle lens and the second corrective component comprises a contact lens.

20. A method according to claim 11, wherein the first corrective component comprises a first spectacle lens and the second corrective component comprises a second spectacle lens.

* * * * *